United States Patent
Acker et al.

(10) Patent No.: US 8,028,695 B2
(45) Date of Patent: Oct. 4, 2011

(54) APPARATUS AND SYSTEM FOR REDUCING MECHANICAL VENTILATOR NOISE

(75) Inventors: Jaron M. Acker, Madison, WI (US); Kristopher J. Bilek, Madison, WI (US); John R. Pinkert, Madison, WI (US); Robert Q. Tham, Middleton, WI (US)

(73) Assignee: The General Electric Company, Schenectady, NY (US)

( * ) Notice: Subject to any disclaimer, the term of this patent is extended or adjusted under 35 U.S.C. 154(b) by 1343 days.

(21) Appl. No.: 11/564,918

(22) Filed: Nov. 30, 2006

(65) Prior Publication Data

US 2008/0127976 A1    Jun. 5, 2008

(51) Int. Cl.
  *A61M 15/00* (2006.01)
  *A61M 15/08* (2006.01)
  *A61M 16/00* (2006.01)
  *A62B 18/08* (2006.01)
  *A61F 11/06* (2006.01)

(52) U.S. Cl. ......... 128/204.18; 128/203.24; 128/204.21; 128/204.22; 128/204.23; 128/206.15; 128/200.24; 128/200.13; 128/203.14; 128/867

(58) Field of Classification Search ............. 128/203.24, 128/204.18, 204.21, 204.22, 204.23, 867, 128/206.15, 200.24, 203.13, 203.14
See application file for complete search history.

(56) References Cited

U.S. PATENT DOCUMENTS 7,694,677 B2 * 4/2010 Tang ................. 128/204.18

OTHER PUBLICATIONS

CaStar "R" Brochure from StarMed Medical Disposals, available at www.starmedspa.com, date accessed: Jan. 18, 2007.
Printout from Rusch webpage for 4Vent http://www.rusch.fr/en/produkte/neuheiten/anaesthesie/4vent_e.php, date accessed: Jan. 18, 2007.
Cavaliere, et al. (2004) "Noise Exposure During Noninvasive Ventilation with a Helmet, a Nasal Mask, and a Facial Mask" Intensive Care Med. 30:1755-1760.
Galia, F. et al. (2005) "Bench Testing of Intensive Care Unit Ventilators for Helmet Non Invasive Ventilation," Respiratory Team, Paris XII University.
CaStar Brochure from StarMed Medical Disposals for The hood for CPAP Therapy, available at www.starmedspa.com, date accessed: Jan. 18, 2007.

* cited by examiner

*Primary Examiner* — Patricia Bianco
*Assistant Examiner* — Nihir Patel
(74) *Attorney, Agent, or Firm* — Andrus, Sceales, Starke & Sawall, LLP

(57) ABSTRACT

A sound dampening apparatus to be disposed in pneumatic connection with a respiratory support system. The respiratory support system may comprise a source of medical gas, a plurality of pneumatic connections and a patient interface. The sound dampening apparatus comprises an inlet, an outlet, and an outer case which forms a sound dampening chamber. As the medical gas flows through the sound dampening apparatus, the noise energy associated with the flow of medical gas is reduced.

15 Claims, 5 Drawing Sheets

APPARATUS AND SYSTEM FOR REDUCING MECHANICAL VENTILATOR NOISE

FIELD OF THE DISCLOSURE

The present disclosure relates to mechanical ventilation systems for the provision of respiratory support to a patient. More specifically, the present disclosure relates to a device and system for reducing the noise generated by the mechanical ventilator that is experienced by the patient.

BACKGROUND OF THE DISCLOSURE

The application of non-invasive ventilation ("NIV") to a patient in need of respiratory support provides the patient with benefits over the use of invasive ventilation techniques such as with an endotracheal (ET) tube. NIV reduces the trauma that a patient experiences in the application of invasive ventilation techniques, for example, intubation. The use of NIV also reduces the risk of ventilator-associated pneumonia and facilitates the weaning of a patient off of mechanical ventilation. Many types of patient interfaces exist to provide a patient with non-invasive ventilation, the most common interfaces utilize a version of a face mask. A drawback of patient interfaces that utilize a face mask is that the patient's mouth is blocked. This reduces the patient's ability to communicate. Furthermore a face mask makes it difficult for the patient to ingest nutrition and/or medication. Also, in the event that a patient vomits, a face mask presents an increased risk of a blocked airway. Finally, patients find discomfort with the use of a mask, both due to the blockage of the patient's mouth as well as the pneumatic pressure that is applied to the patient's face through the patient interface.

In order to address these issues, a pneumatic helmet has been used to deliver respiratory support to a patient. The helmet secures around the patient's neck and/or shoulders to provide a pneumatically sealed compartment about the patient's head. The helmet is typically constructed of a flexible and transparent material such that the patient retains the freedom to move his or her head and to communicate verbally and non-verbally through the material of the helmet. The benefits of the helmet include improved patient communication and a greater sense of freedom experienced by the patient.

However, it has been identified that the noise within the confined space of a non-invasive ventilation helmet can reach discomforting and even dangerous levels. Studies have measured the noise inside the helmet to exceed 100 dB. While OSHA workplace safety standards suggest limiting exposure to noises above 100 dB to less than 2 hours at a time, the patient may be exposed to these noise levels throughout the duration of the respiratory support, which may last days or weeks. This compounds any ill effects from the exposure to the loud noises. The loud noises also contribute to the discomfort that the patient associates with receiving respiratory support. Patient discomfort can lead to an overall unfavorable care experience, and can lead to adverse physiological effects such as increased heart rate or blood pressure. Furthermore excessive noise in the helmet may prevent the patient from falling asleep, and/or staying asleep, thereby reducing the patient's ability to recuperate.

The noise within the helmet has many sources within the mechanical ventilator. One source of noise is the medical gas supply source. Mechanical ventilators typically have one of two different types of systems for providing a flow of medical gas. First, the flow of medical gas may be generated by a compressor or pump that takes in ambient air and delivers it at the desired flow rate to the patient. This compressor or pump is typically loud in its operation, resulting in this noise being transmitted to the helmet. Secondly, the flow of medical gas may be received by the mechanical ventilator from a wall supply of high pressure medical gas supplied to the hospital room. In this system, a pressure regulator in the ventilator reduces the wall gas pressure to deliver a flow of medical gas at the desired flow rate. The reduction of the wall gas pressure is loud and this noise is transmitted through the breathing circuit directly to the patient via the helmet. Therefore, both sources of medical gas commonly used by medical ventilators cause noise in the NIV helmet. Alternatively, the flow of medical gas may be supplied by a different apparatus such as a stand alone CPAP device, or a manual ventilation bag. However, the noise within the patient interface is also an issue with these sources of medical gas flow. Furthermore, it is not uncommon for the plastic tubing that forms the breathing circuit to be corrugated in design to promote flexibility and reduce kinking. However, the corrugated tubing causes turbulence in the flow of medical gas, therefore creating additional noise in the breathing circuit and the NIV helmet.

Attempts have been made to reduce the noise levels within the helmet by modifying the pressure and flow rates of the medical gases provided to the patient through the helmet. However, this technique has not shown a meaningful effect on reducing the noise within the helmet. Alternatively, it has been attempted to reduce the noise in the helmet by including one or more filters, such as a heat and moisture exchange (HME) filter, in an attempt to attenuate the noise associated with the provision of medical gas to the helmet. However, this too did not produce a meaningful decrease in the noise experienced inside of the helmet.

The lack of effectiveness of these attempts to reduce noise may be due to the fact that the noise is the result of inherent features of standard mechanical ventilator components. Furthermore, the HME filter is not designed to maximize any sound-attenuating properties that the HME filter may have. While a HME filter comprises a core of foam or other filter material that the medical gas must flow through, the amount of material present is not sufficient to dampen the noise effectively. If the filter material of the HME filter were modified or the amount of the filter material increased, the HME filter would present an increased resistance to the flow of medical gas being provided to the patient. Increased resistance within the breathing circuit of a mechanical ventilation system is undesirable as this resistance must be overcome by higher pressures within the breathing circuit and the resistance affects the waveform of medical gas that is actually received by the patient.

Therefore, it is desirable in the field of non-invasive mechanical ventilation to provide a sound dampening apparatus for a mechanical ventilation system such that the sound dampening apparatus reduces the noise within a non-invasive helmet and does not substantially increase the resistance of the breathing circuit.

BRIEF DESCRIPTION THE DISCLOSURE

The present disclosure relates to a device and system for attenuating the noise experienced by a patient that is receiving non-invasive respiratory support via a mechanical ventilator and a pneumatic helmet patient interface.

In an embodiment, a sound dampening apparatus comprises an inlet and an outlet, the inlet and the outlet being connected by an outer casing forming a sound dampening chamber.

In a further embodiment, the sound dampening apparatus comprises a sound absorbent material disposed within the sound dampening chamber.

In a still further embodiment, a sound dampening apparatus comprises a structure for diverting the flow of medical gas such that the flow of medical gas contacts the sound absorbent material.

In another embodiment, a mechanical ventilation system comprises a source of medical gas and a patient connection, the source of medical gas and the patient interface being pneumatically connected by a plurality of pneumatic conduits and a sound dampening apparatus is connected to at least one conduit between the medical gas source and the patient interface.

DETAILED DESCRIPTION

Figure 1:
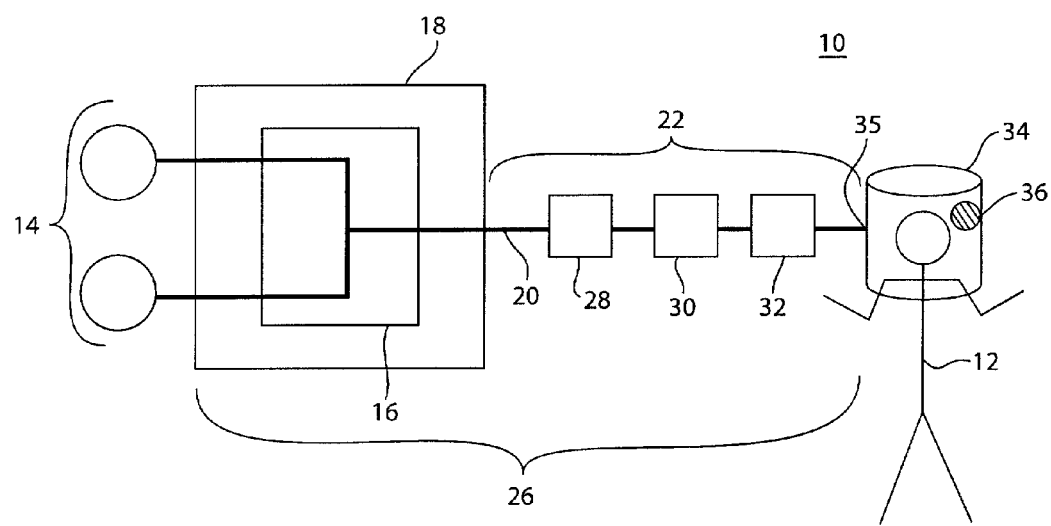
FIG. 1 is a schematic diagram of a system for providing non-invasive mechanical ventilation.

FIG. 1 depicts a schematic diagram of a mechanical ventilation system 10 for providing respiratory support to a patient 12. The system 10 comprises a series of pneumatic conduits and modules 26 that form a pneumatic connection between a medical gas source 14 and the patient 12. The medical gas source 14 is connected to a manifold 16 of a mechanical ventilator 18. The manifold 16 serves to combine the constituent gases that are provided from the medical gas source 14 into the desired medical gas that is to be delivered to the patient 12. Alternatively, the mechanical ventilator 18 may be replaced by an alternative device for controlling the flow of medical gas. This alternative device may comprise a CPAP device connected to the source of medical gas or a manually operated ventilation bag.

The term "medical gas" as used in this application refers to any gas or combination of gases that is delivered to a patient in a clinical setting. Most commonly, the medical gas delivered to the patient is air. In other instances, the air is combined with a supplemental gas or gases which provide increased physiological or therapeutic support with the mechanical ventilation. The supplemental gases may include gases such as oxygen, helium, nitrous oxide, an anesthetic agent, or a drug aerosol. However, this list is merely exemplary of the types of supplemental gases that may be used in accordance with the present invention and is not intended to be limiting to the scope of the present invention.

Once the gases from the medical gas source 14 have been mixed in the manifold 16, the medical gas is directed into the inspiratory limb 20 of the breathing circuit 22. Before the medical gas is delivered to the patient 12, the medical gas may pass through any number of modules. These modules may include a gas sampling module 28, which may be a chamber to which a side stream of a gas sampling device such as an MGAS module as available from GE Healthcare, is attached. The medical gas may pass through a heat and moisture exchange (HME) filter 30 to control the humidity and temperature of the medical gas that is delivered to the patient 12. Many other modules may be used in the system 10 such as a humidifier or a moisture trap; however, the described modules are not intended to be limiting on the scope of embodiments of the mechanical ventilation system 10.

Next, the medical gas may travel through a sound dampening apparatus 32 and into the patient interface 34 that facilitates the delivery of the medical gas to the patient 12. It is understood that the sound dampening apparatus 32 may be located anywhere in the system 10 along the plurality of conduit sections 26. The sound dampening apparatus 32 is not limited to its location within the system 10, only that it requires that the medical gas be flowing through it. The patient interface 34 may be a pneumatic helmet as depicted, but the patient interface 34 may also be any similarly situated patient interface 34 for delivering medical gas to a patient 12. In an embodiment, the patient interface 34 forms a pneumatic seal around the neck of the patient 12. In a further embodiment, the patient interface 34 forms a pneumatic seal around the shoulders of the patient 12.

The mechanical ventilator 18 delivers a flow of medical gas into the patient interface 34 such that the pressure within the patient interface 34 rises to the level needed to deliver respiratory support to the patient 12. When the mechanical ventilator 18 reduces the pressure within the patient interface 34, the patient enters an expiratory phase and the expired gas exits the patient interface 34 through an expiratory vent 36. In an embodiment of the patient interface 34, vent 36 is located opposite the connection 35 between the breathing circuit 22 and the patient interface 34. A bias flow through the plurality of conduit sections 26 may help to direct the patient's expired breath out of the expiratory vent 36.

Alternatively, the patient interface may comprise an expiratory part (not depicted) that is connected to an expiratory limb (not depicted) that directs the expired breath back to the mechanical ventilator 18. This embodiment may be used in situations where it is designed to direct the expired breath to a scavenging system, or if the positive end expiratory pressure (PEEP) of the patient is to be controlled by the mechanical ventilator 18.

Figure 2:
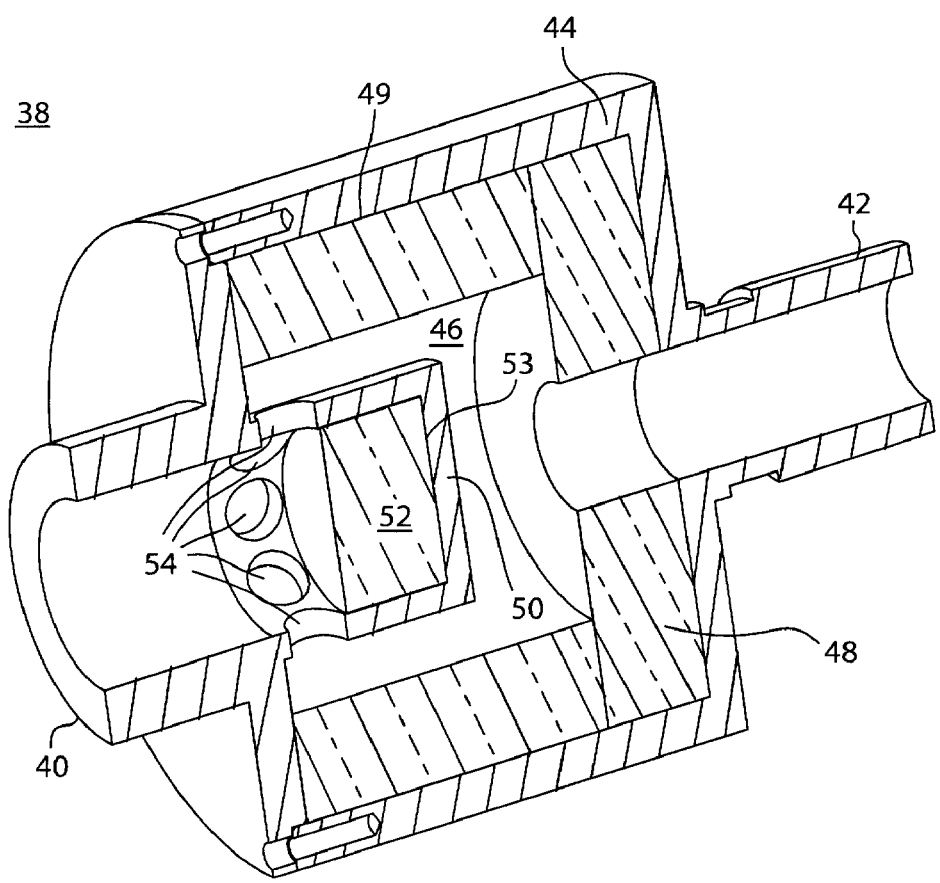
FIG. 2 is a depiction of an embodiment of a unidirectional flow sound dampening apparatus.

FIG. 2 depicts an embodiment of the sound dampening apparatus. In this embodiment, the sound dampening apparatus is a muffler 38 for the reduction of noise within the mechanical ventilation system 10. The muffler 38 may comprise an inlet 40 and an outlet 42 that are pneumatically connected such that medical gas may enter the muffler 38 through the inlet 40 and exit through the outlet 42. The inlet 40 and the outlet 42 are connected by an outer case 44. The inlet 40, outlet 42, and the outer case 44 may be all made from the same material, which in any embodiment may be a plastic, polycarbonate, a resin, aluminum, stainless steel, or any other suitable material. The material selection may be dependent upon the location within the system 10 that the muffler 38 is located.

The outer case 44 comprises an inner surface 49 and forms a sound dampening chamber 46 that provides the pneumatic connection between the inlet 40 and the outlet 42. The muffler 38 may further comprise a layer of a sound absorbent material 48. The sound absorbent material 48 may be disposed inwardly from the outer case 44 against the inner surface 49 such that the sound dampening chamber 46 is defined, at least in part by the sound absorbent material 48. The sound absorbent material 48 may be disposed against the inner surface 49 such that the sound absorbent material is held in place by friction, form-fitting or an adhesive; however, this is not intended to be limiting on the scope of the sound absorbent material, as other suitable means for holding materials in place may be used.

As medical gas flows into the muffler 38 via the inlet 40, the medical gas contacts the sound absorbent material and the sound absorbent material 48 absorbs a substantial amount of the energy of the sound waves associated with the medical gas. The sound absorbent material 48 may be disposed to reduce sound at the frequencies commonly associated with the operation of a mechanical ventilator such that the sound absorbent material 48 is effective in removing the mechanical ventilator noise from the medical gas that is delivered to the patient. In one embodiment, the sound absorbent material is a foam material that is removably adhered to the inner surface 49 of outer case 44; however, many other types of sound absorbent material are suitable for use in other embodiments of the muffler 38.

The muffler 38 may further comprise an end piece 50 disposed at one end of the inlet 40. Preferably, the end piece 50 extends into the sound dampening chamber 46 as defined by the outer case 44 and the sound absorbent material 48. The end piece 50 further comprises an inner surface 53, an additional sound absorbent material 52 being adjacent to the inner surface 53. The additional sound absorbent material 52 may be the same sound absorbent material as 48, but may alternatively be a different material. In an embodiment of the muffler 38 comprising the end piece 50, the medical gas flows into the inlet 40 and contacts the sound absorbent material 52. In contacting the sound absorbent material, sound energy is removed from the flow of medical gas, while the flow of medical gas is directed out of the inlet 40 through a first plurality of passages 54. The passages 54 further direct the flow of medical gas into the sound dampening chamber 46 and into contact with the sound absorbent material 48, thus removing more sound energy from the flow of medical gas. The medical gas is then further directed out of the sound dampening chamber 46 and through the outlet 42 to continue through the plurality of conduit sections to be delivered to the patient by the patient interface 34.

Figure 3:
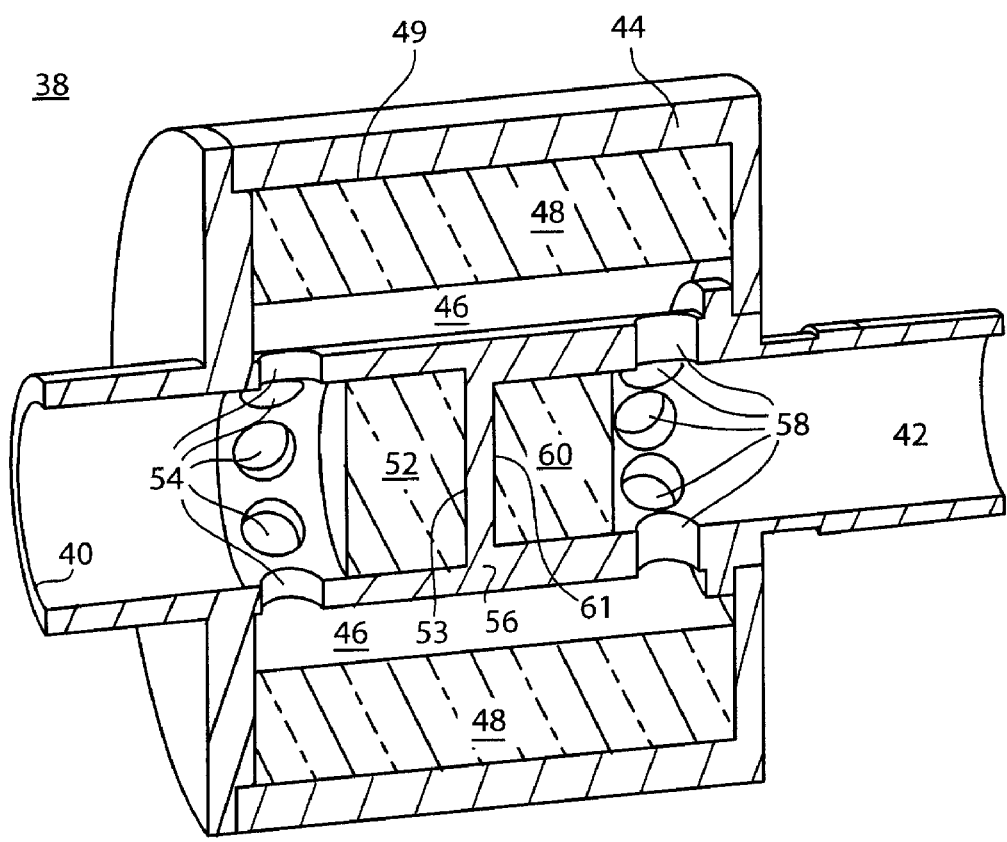
FIG. 3 is a depiction of an embodiment of a bidirectional flow sound dampening apparatus.

FIG. 3 is an embodiment of the muffler 38 that is disposed for bi-directional flow through the muffler 38. Muffler 38 comprises an inlet 40 and an outlet 42 that are physically connected by an outer case 44 and a common end piece 56. The common end piece comprises inner surfaces 53 and 61 respectively. The inlet 40 and the outlet 42 are pneumatically connected by a sound dampening chamber 46 that comprises the space between the outer case 44 and the common end piece 56. A sound absorbent material 48 is adjacent to the inner surface 49 of the outer case 44. The sound absorbent material 48 may comprise any suitable material for the absorption of sound wave energy.

In operation, the medical gas may flow into the inlet 40 and into contact with the sound absorbent material 52 adjacent to the inner surface 53 of the common end piece 56. The sound absorbent material 52 directs the flow of medical gas through the plurality of passages 54 into the sound dampening chamber 46. The flow of medical gas in the sound dampening chamber 46 contacts the sound absorbent material 48 such that a substantial amount of the noise that is associated with the medical gas is removed before the medical gas flows through a second plurality of passages 58 and out through the outlet 42.

The embodiment of the muffler 38 depicted in FIG. 3 differs from the embodiment of the muffler 38 depicted in FIG. 2 in that the muffler 38 may be attached to any of the plurality of conduit sections 26 in the opposite orientation such that the outlet 42 receives the flow of medical gas and the inlet 40 expels the flow of medical gas. In the reverse orientation, the flow of medical gas enters the outlet 42 where it contacts sound absorbent material 60 that is adjacent to the inner surface 61 of the common end piece 56. The sound absorbent material 60 directs the flow of medical gas through the second plurality of passages 58 and into the sound dampening chamber 46, while the sound absorbent material 60 also removes sound energy from the flow of medical gas. The sound absorbent material 48 removes a substantial amount of the noise energy from the flow of medical gas before the flow of medical gas flows through the first plurality of passages 54 and out the inlet 40.

Figure 4:
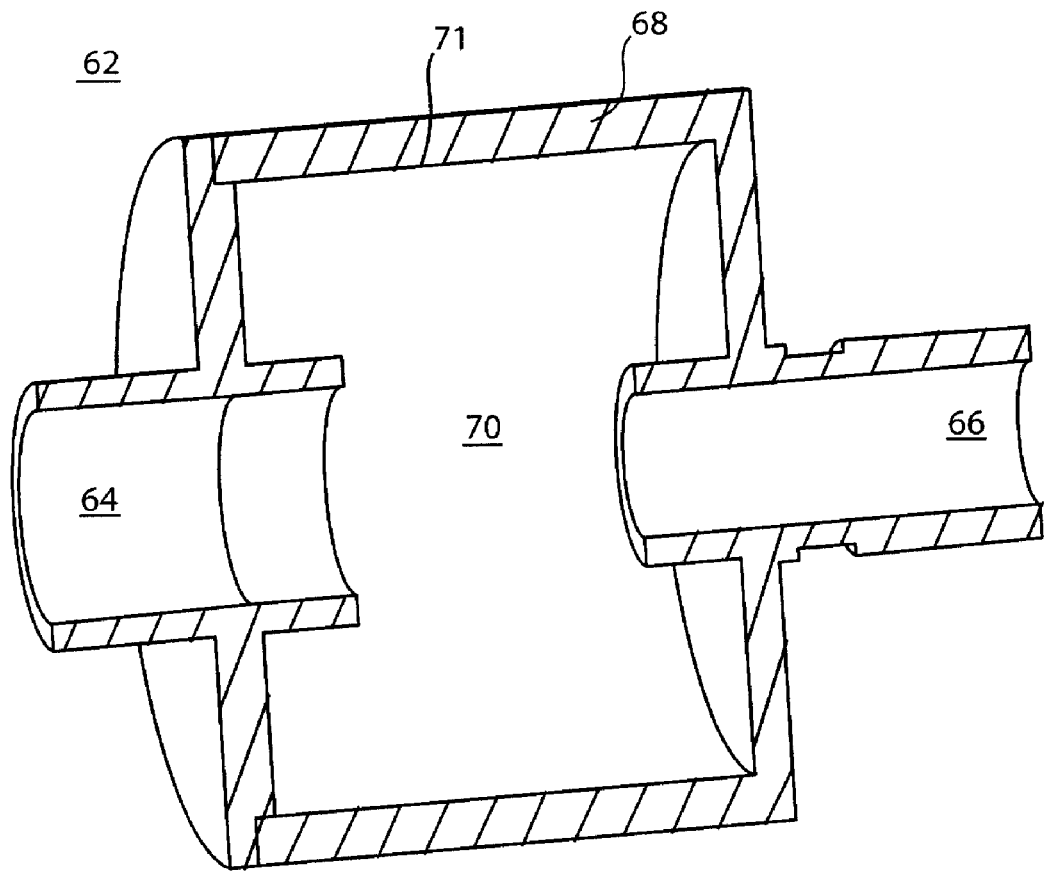
FIG. 4 is a depiction of an embodiment of a resonator-type sound dampening apparatus.

FIG. 4 is an embodiment where the sound dampening apparatus is a resonator 62. In this embodiment, the resonator 62 comprises an inlet 64 and an outlet 66 that are physically connected by an outer case 68. The inlet 64, outlet 66, and outer case 68 define a sound dampening chamber 70. In operation, the resonator 62 reduces the noise in the flow of medical gas by reflecting the noise back on itself. As medical gas flows into the sound dampening chamber 70 through the inlet 64, the sound waves reflect off of the inner surfaces 71 of the outer case 68 and are directed back on the sound waves entering the sound dampening chamber 70 with the continued flow of medical gas. Therefore, the medical gas continues to flow through the resonator 62 and exits the sound dampening chamber 70 through the outlet 66 while the noise energy associated with the flow of medical gas is cancelled by the reflected noise energy.

Figure 5:
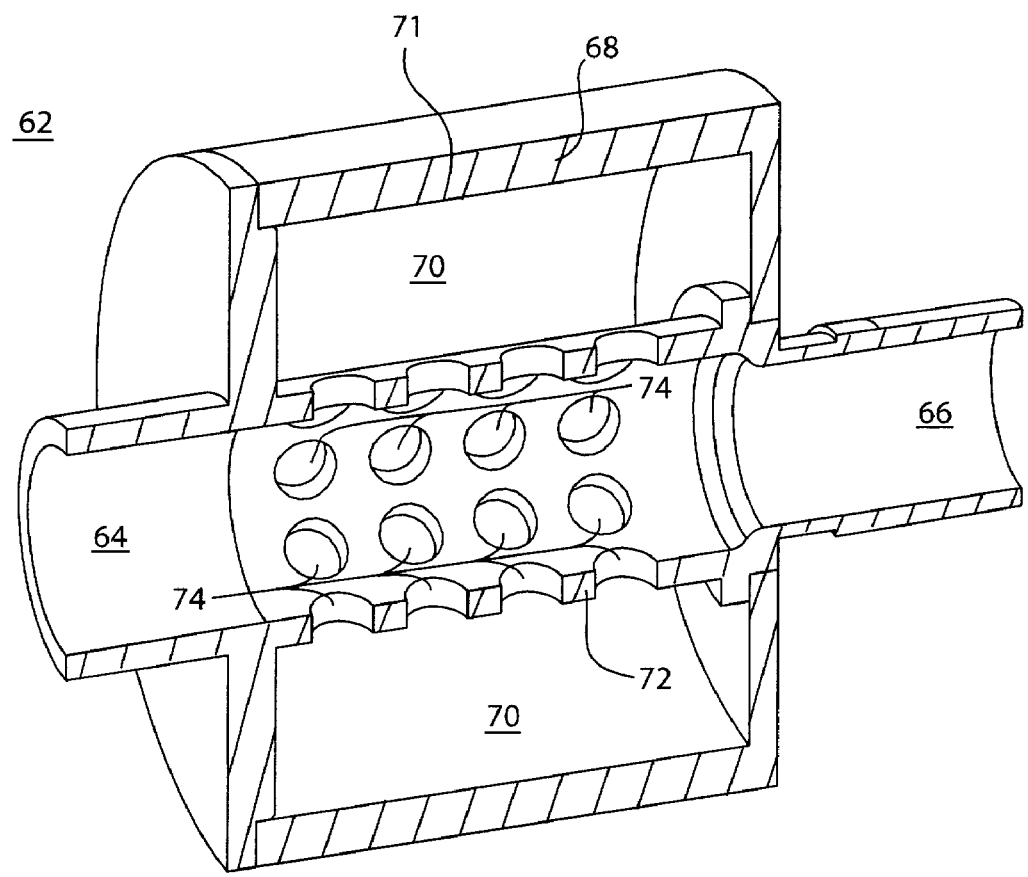
FIG. 5 is a depiction of an alternative embodiment of a resonator-type sound dampening apparatus.

FIG. 5 depicts an alternative embodiment of the resonator 62. This resonator 62 also comprises an inlet 64 and an outlet 66 that are physically connected by a outer case 68 that defines a sound dampening chamber 70. However, the in the embodiment of the resonator 62 depicted in FIG. 5, the inlet 64 and the 66 are further physically connected by a perforated core 72. The perforated core 72 comprises a plurality of perforations 74. The perforated core 72 further helps the resonator 62 in its sound canceling function, thus improving the noise reduction. In operation, the medical gas flows through the inlet 64 and out the outlet 66. The noise associated with the flow of medical gas is only allowed to leave the perforated core 72 at a roughly orthogonal direction to the flow of medical gas. The noise energy reflects off of the inner surface 71 of the outer case 68 and back towards the perforated core 72 wherein the reflected noise energy is only allowed to enter the perforated core 72 at a roughly orthogonal angle to the flow of medical gas, such that the reflected sound energy is approximately 180 degrees out of phase with the noise energy still associated with the flow of medical gas. The introduction of sound energy that is 180 degrees out of phase with the sound energy that would normally be delivered to the patient helps to more effectively reduce the auditory noise that reaches the patient along with the flow of medical gas.

In an alternative embodiment, the sound dampening apparatus 32 may comprise a water trap (not depicted). The water trap may be a gravity-based water trap disposed to reduce moisture build up within the apparatus 32, to ensure that the apparatus 32 does not become moisture logged. A moisture logged apparatus 32 may reduce the effectiveness of the apparatus 32. Alternatively, the apparatus 32 may be placed in the mechanical ventilation system at a location proximal to the patient from a separate water trap module (not depicted) such that a substantial amount of the moisture in the medical gas has already been removed before entering the apparatus 32. Alternatively, in an embodiment of the mechanical ventilation system that comprises a humidifier module (not depicted), the apparatus 32 may be connected to the mechanical ventilation system at a location that is more distal from the patient than the humidifier, such that the medical gas travels through the apparatus 32 before the medical gas is humidified by the humidifier.

In a further embodiment, the apparatus 32 is built into any one of the modules associated with the mechanical ventilation system, such as the patient interface 34, a HME filter 30, a gas sampling module 28, or any component of the breathing circuit 22.

In a still further embodiment, if the apparatus 32 is an integral part of a disposable module of the mechanical ventilation system 10, the apparatus 32 may be constructed in such a fashion and out of such materials that the apparatus 32 is also considered to be disposable. In this embodiment, the apparatus 32 may comprise material known in the art for the construction of a disposable medical apparatus, and the sound absorbent material may similarity be of a disposable type material.

In an alternative embodiment, if the apparatus 32 is integral with a reusable module of the mechanical ventilation system 10, the apparatus 32 may be constructed from materials that are known in the art for use in reusable medical devices. Apparatus 32 may be constructed such that the apparatus 32 may be sterilized by autoclaving or another commonly used sterilization method.

In a still further embodiment, the inlet 40, outlet 42, and outer casing 44 are constructed of a material such that these component are reusable, while the absorbent material 48, 52 may be constructed from a disposable material, such that the sound absorbent material 48, 52 may be discarded after use, while the inlet 40, outlet 42 and outer casing 44 are sterilized for another use with replaced sound absorbent material.

In an alternative embodiment, the apparatus 32 may be attached to, or an integral component of the mechanical ventilator 18. In this embodiment, the integral component of the mechanical ventilator 18 may be the manifold 16.

In an embodiment of the apparatus 32, the apparatus 32 may be unidirectional such that the medical gas must flow in the inlet 40 and out the outlet 42 for the sound dampening function of the apparatus 32 to work. In this embodiment, the apparatus 32 may comprise mechanical barriers (not depicted) to prevent the improper connection of the apparatus 32 in the mechanical ventilation system 10. The mechanical barriers may comprise physical differences in the inlet 40 and the outlet 42 such that the apparatus 32 may be only connected in the proper orientation.

Embodiments of the apparatus present the advantage of reducing the noise that the patient experiences when respiratory support is delivered through the patient connection. This reduces the patient's discomfort that is associated with receiving mechanical respiratory support, while also reducing any harm that may occur to the patient's hearing from exposure to the loud noises associated with delivery of respiratory support through the patient connection. Furthermore, by reducing the noise that the patient experiences, the patient's ability to communicate with clinicians and/or family while receiving respiratory support is improved. The patient may more easily hear auditory communication from clinicians and/or family. Embodiments of the apparatus also present the advantage of reducing the noise experienced by the patient at the patient interface while also not increasing the pneumatic resistance to delivering medical gas to the patient. Alternatively, the apparatus does not substantially increase the pneumatic resistance to the provision of medical gas to the patient via the mechanical ventilation system.

Embodiments of the apparatus are advantageous as they present a cost effective solution to reducing the noise experienced by a patient when the patient receives respiratory support via a patient connection. Specifically, embodiments of the apparatus may be implemented with existing mechanical ventilators, such that a healthcare provider need not replace the mechanical ventilator in order to receive the benefit of reducing the noise experienced by the patient.

This written description uses examples to disclose features of the embodiments, including the best mode, and also to enable any person skilled in the art to make and use the invention. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Various alternatives and embodiments are contemplated as being with in the scope of the following claims, particularly pointing out and distinctly claiming the subject matter regarded as the invention.

What is claimed is:

1. A mechanical ventilation system for providing medical gas to a patient, the mechanical ventilation system comprising:
   a source of medical gas;
   a patient connection to facilitate the delivery of the medical gas to the patient wherein the patient connection is a helmet pneumatically connected about a head of the patient;
   a conduit connecting the source of medical gas to the patient connection, the conduit comprising at least one conduit section or module;
   means for controlling a flow of medical gas, the means receives the medical gas from the source of medical gas, controls the flow of the medical gas. and imparts a noise component on the flow of the medical gas; and
   a sound dampening apparatus connected intermediate the patient connection and the means for controlling the flow of medical gas, the sound dampening apparatus comprising an inlet, an outlet, and an outer case physically connecting the inlet to the outlet and forming a sound dampening chamber pneumatically connecting the inlet to the outlet;
   wherein the sound dampening apparatus reduces the noise experienced by the patient due to the provision of the medical gas without substantially increasing the pneumatic resistance between the source of medical gas and the patient connection.

2. The mechanical ventilation system of claim 1 further comprising sound absorbent material disposed in the sound dampening chamber, wherein the inlet comprises an end piece and a plurality of passages for directing the medical gas into the sound dampening chamber.

3. The mechanical ventilation system of claim 1 wherein the apparatus is connected to the patient connection.

4. The mechanical ventilation system of claim 1 wherein the means for controlling the flow of medical gas is a ventilator, wherein the apparatus is connected intermediate the ventilator and the patient connection.

5. The mechanical ventilation system of claim 4 further comprising a manifold associated with the ventilator, wherein the apparatus is connected to the manifold.

6. The mechanical ventilation system of claim 1, wherein the sound dampening apparatus reduces the noise component imparted on the flow of the medical gas by the means for controlling the flow of medical gas as perceived by the patient inside the patient connection.

7. The mechanical ventilation system of claim 1, wherein the sound dampening apparatus comprises a perforated core connecting the inlet and the outlet.

8. The mechanical ventilation system of claim 7, wherein at least one conduit section is selected from the list comprising: a manifold, a Y-connector, a moisture trap, a humidifier, a gas sampling module, and a heat and moisture exchange filter.

9. A mechanical ventilation system for providing medical gas to a patient, the mechanical ventilation system comprising:
- a source of medical gas;
- a patient connection to facilitate the delivery of the medical gas to the patient wherein the patient connection is a helmet configured to be pneumatically sealed about a head of the patient;
- a conduit connecting the source of medical gas to the patient connection, the conduit comprising at least one conduit section or module;
- a ventilator that receives medical gas from the source of medical gas, controls the medical gas, and imparts a noise component on the flow of medical gas; and
- a sound dampening apparatus connected intermediate the patient connection and the ventilator, the apparatus comprising an inlet, an outlet, and an outer case physically connecting the inlet to the outlet and forming a sound dampening chamber pneumatically connecting the inlet to the outlet;
- wherein the apparatus reduces the noise experienced by the patient due to the provision of the medical gas without substantially increasing the pneumatic resistance between the source of medical gas and the patient connection.

10. The medical ventilation system of claim 9 further comprising sound absorbent material disposed in the sound dampening chamber, wherein the inlet comprises an end piece and a plurality of passages for directing the medical gas into the sound dampening chamber.

11. The mechanical ventilation system of claim 9, wherein the sound dampening apparatus is connected to the patient connection.

12. The mechanical ventilation system of claim 9 further comprising a manifold associated with the ventilator, wherein the sound dampening apparatus is connected to the manifold.

13. The mechanical ventilation system of claim 9, wherein the sound dampening apparatus reduces the noise component imparted on the flow of the medical gas by the ventilator as perceived by the patient inside the patient connection.

14. The mechanical ventilation system of claim 9, wherein the sound dampening apparatus comprises a perforated core connecting the inlet and the outlet.

15. The mechanical ventilation system of claim 14, wherein at least one conduit section is selected from the list comprising: a manifold, a Y-connector, a moisture trap, a humidifier, a gas sampling module, and a heat and moisture exchange filter.

* * * * *